United States Patent
List et al.

(10) Patent No.: US 9,932,305 B2
(45) Date of Patent: Apr. 3, 2018

(54) PROCESS FOR THE ASYMMETRIC OXIDATION OF ORGANIC COMPOUNDS WITH PEROXIDES IN THE PRESENCE OF A CHIRAL ACID CATALYST

(71) Applicant: STUDIENGESELLSCHAFT KOHLE MBH, Mülheim an der Ruhr (DE)

(72) Inventors: Benjamin List, Mülheim an der Ruhr (DE); Ilija Coric, Mülheim an der Ruhr (DE); Saihu Liao, Fujian (CN)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 14/371,333

(22) PCT Filed: Jan. 8, 2013

(86) PCT No.: PCT/EP2013/050190
§ 371 (c)(1),
(2) Date: Jul. 9, 2014

(87) PCT Pub. No.: WO2013/104605
PCT Pub. Date: Jul. 18, 2013

(65) Prior Publication Data
US 2015/0005527 A1  Jan. 1, 2015

(30) Foreign Application Priority Data

Jan. 10, 2012 (GB) ................................ 12150663.8
Mar. 7, 2012 (EP) .................................... 12158469

(51) Int. Cl.
| | | |
|---|---|---|
| *C07C 315/02* | (2006.01) | |
| *B01J 31/02* | (2006.01) | |
| *C07B 53/00* | (2006.01) | |
| *C07B 45/04* | (2006.01) | |
| *C07D 493/10* | (2006.01) | |
| *C07F 9/6571* | (2006.01) | |
| *C07F 9/6574* | (2006.01) | |

(52) U.S. Cl.
CPC ......... *C07C 315/02* (2013.01); *B01J 31/0258* (2013.01); *B01J 31/0264* (2013.01); *C07B 45/04* (2013.01); *C07B 53/00* (2013.01); *C07D 493/10* (2013.01); *C07F 9/65744* (2013.01); *C07F 9/657154* (2013.01); *B01J 2231/70* (2013.01); *C07B 2200/07* (2013.01); *C07C 2601/14* (2017.05); *C07C 2602/08* (2017.05)

(58) Field of Classification Search
CPC .. C07C 315/02; B01J 31/0201; B01J 31/0239
See application file for complete search history.

(56) References Cited

U.S. PATENT DOCUMENTS

2010/0094037 A1  4/2010  Katsuki et al.

FOREIGN PATENT DOCUMENTS

| EP | 1 623 971 A1 | 2/2006 |
|---|---|---|
| WO | 2008 152462 A1 | 12/2008 |

OTHER PUBLICATIONS

Allen et al. "Juliá-Colonna asymmetric epoxidation reactions under non-aqueous conditions: rapid, highly regio- and stereo-selective transformations using a cheap, recyclable catalyst" J. Chem. Soc. Perkin Trans. 1 1998, 3171-3179.*
Shinkai et al. "Enantioselective Oxidation of Sulphides with Chiral 4a-Hydroperoxyflavin" J. Chem. Soc. Chem. Commun. 1988, 21, 1399-1401.*
Kagan et al. "Asymmetric Oxidation of Sulfides" in Catalytic Asymm. Synth. 2nd Edition. Ed. Iwao Ojima. Wiley, 2000. pp. 327-356.*
Dohi, T. "Recycling and Catalytic Approaches for the Development of a Rare-Metal-Free Synthetic Method Using Hypervalent Iodine Reagent" Chem. Pharm. Bull. 2010, 58, 135-142.*
Wang et al. "Catalytic Asymmetric Epoxidation of Cyclic Enones" J. Am. Chem. Soc. 2008, 130, 6070-6071.*
Katsuki, T. "Asymmetric Oxidation with Hydrogen Peroxide, an Effective and Versatile Oxidant" Pharm. Process Chem. Edited by Takayaki Shioiri et al. Wiley, 2011. pp. 59-72.*
Kagan, H. B. "Oxidation of heteroatoms: asymmetric oxidation of sulfides and selenides" Asymmetric Oxidation Reactions 2001, pp. 153-170.*
Berkessel et al. Tetrahedron: Asymmetry 1996, 7, 671-672.*
International Search Report of corresponding international application PCT/EP2013/050190 dated Aug. 7, 2013.
Liu, et al; "Chiral phosphoric acid-catalyzed asymmetric oxidation of aryl alkyl sulfides and aldehyde-derived 1,3-dithianes: using aqueous hydrogen peroxide as the terminal oxidant"; Advances Synthesis & Catalysis, vol. 354, No. 6, Apr. 2012, 1012-1022.
Legros, et al; "Applications of catalytic asymmetric sulfide oxidations to the syntheses of biologically active sulfoxides"; Advanced Synthesis and Catalysis, vol. 347, Jan. 2005, 19-31.
Zheng et al; "Chiral phosphoric acid catalyzed peroxidation of imines"; Agenwandte Chemie International Edition, vol. 49, No. 37, Sep. 2010, 6589-6591.
Komatsu et al; "Catalytic asymmetric oxidation of sulfides to sulfoxides with tert-butyl hydroperoxide using binaphthol as a chiral auxiliary"; Journal of Organic Chemistry, vol. 58, No. 17, Jan. 1993, 4529-4533.

(Continued)

*Primary Examiner* — Amanda L Aguirre
(74) *Attorney, Agent, or Firm* — Norris McLaughlin & Marcus, P.A.

(57) ABSTRACT

The present invention relates to a process for the asymmetric oxidation of nucleophilic organic compounds, particularly metal-free, with peroxide compounds in the presence of a chiral Brønsted acid catalyst. In one detail, the present invention relates to a process for enantioselective sulfoxidation of thiocompounds with peroxide compounds in the presence of a chiral imidodiphosphate catalyst. In another detail, the present invention relates to a process for enantioselective sulfoxidation of thiocompounds with peroxide compounds in the presence of a chiral phosphoric acid catalyst.

15 Claims, 1 Drawing Sheet

(56) References Cited

OTHER PUBLICATIONS

Davis et al; "(−)-.alpha., .alpha.-dichlorocamphorsulfonyloxaziridine: a superior reagent for the asymmetric oxidation of sulfides to sulfoxides"; Journal of the American Chemical Society, vol. 111, No. 15, Jul. 1989, 5964-5965.
Page et al; "Asymmetric sulfoxidation using [(3,3-dimethoxycamphoryl)sulfonyl]oxaziridine"; Tetrahedron Asymmetry, vol. 6, No. 12, Dec. 1995, 2911-2914.

* cited by examiner chiral Brønsted acid (HX*)
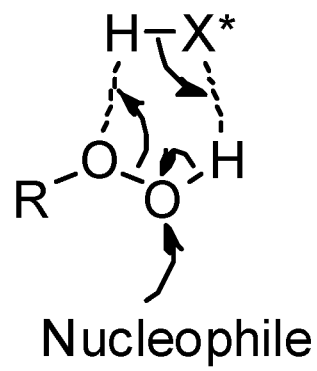
Nucleophile

PROCESS FOR THE ASYMMETRIC OXIDATION OF ORGANIC COMPOUNDS WITH PEROXIDES IN THE PRESENCE OF A CHIRAL ACID CATALYST

This application is a 371 of PCT/EP2013/050190, filed Jan. 8, 2013, which claims foreign priority benefit under 35 U.S.C. § 119 of the European Patent Application Nos. 12150663.8, filed Jan. 10, 2012, and 12158469.2, filed Mar. 7, 2012, the disclosures of which are incorporated herein by reference.

The present invention relates to a process for the asymmetric oxidation of nucleophilic organic compounds, particularly metal-free, with peroxide compounds in the presence of a chiral Brønsted acid catalyst. Said process is distinct from known reactions which require an electrophilic organic compound for a reaction with a peroxide compound in the presence of a chiral Brønsted acid catalyst (Angew. Chem. Int. Ed. 2010, 49, 6589-6591; Angew. Chem. Int. Ed. 2008, 47, 8112-8115). The present invention exploits peroxide compounds as direct electrophilic sources of oxygen atom, while in the prior art peroxide compounds are exploited as nucleophiles.

In one detail, the present invention relates to a process for enantioselective sulfoxidation of thiocompounds with peroxide compounds in the presence of a chiral imidodiphosphate catalyst. In another detail, the present invention relates to a process for enantioselective sulfoxidation of thiocompounds with peroxide compounds in the presence of a chiral phosphoric acid catalyst.

Asymmetric oxidations of organic compounds, in particular those including oxygen atom transfer to the substrate, are highly valuable transformations for accessing chiral molecules. Both, enzymes and numerous artificial catalysts employ metals to facilitate these types of reactions.

Hydrogen peroxide is next to oxygen the most attractive oxidant, with the waste produced after the reaction being only water. It is produced on a million ton scale each year, and widely available in the form of safe aqueous solutions. Unsurprisingly, significant efforts have been undertaken to utilize $H_2O_2$ for oxidations in organic chemistry. In metal catalysis it is used as a terminal oxidant with actual oxidizing intermediates being, for example, metal-oxo and metal-peroxo species.

Chiral sulfoxides are widely used as intermediates, auxiliaries, and ligands in modern organic synthesis, and they are also a common and perhaps underappreciated substructure of many biologically active molecules and pharmaceuticals such as Omeprazole, Esomeprazole and Modafinil (R. Bentley, Chem. Soc. Rev. 2005, 34, 609-623; J. Legros, J. R. Dehli, C. Bolm, Adv. Synth. Catal. 2005, 347, 19-31). Of the methods for the synthesis of enantioenriched sulfoxides (e.g. resolution, substrate or reagent-controlled synthesis), the enantioselective catalytic oxidation of sulfides is the most efficient and straightforward approach. Since the first catalytic system was reported in 1984 by Kagan (P. Pitchen, E. Duñach, M. N. Deshmukh, H. B. Kagan, J. Am. Chem. Soc. 1984, 106, 8188-8193) and Modena (F. DiFuria, G. Modena, R. Seraglia, Synthesis 1984, 325-326), using modified Sharpless epoxidation catalysts, several elegant metal-based enantioselective sulfoxidation reactions of sulfides have been developed during the last three decades.

However, such metal-based systems usually suffer from some limitations like metal contamination, over-oxidation, a limited substrate scope etc. In contrast to the significant progress in the metal catalysis, the development of organocatalytic methods is still in its infancy, although organocatalysis has experienced an explosive progress and expansion during the last decade.

Among metal-free methods, high enantioselectivity has been achieved by using chiral imines or oxaziridiniums, but these transformations require stoichiometric amounts of the chiral reagents and the corresponding catalytic systems are relatively less efficient. Considering the importance of optically pure sulfoxides in synthetic and medicinal chemistry, a general, metal-free, and highly enantioselective catalytic sulfoxidation reaction of sulfides is highly desirable.

Thus, the inventors have developed a novel and metal-free method for the enantioselective oxidation of sulfides such as thioethers. Though it is quite difficult to activate simple thioethers via covalent or H-bonding activation, which are two most common activation models in organocatalysis, due to the lack of a site or a functional group to establish an efficient interaction between the organic catalysts and the sulfides, the inventors have found out that a viable approach was given by the activation of oxidants and that an asymmetric version of the sulfoxidation reaction was achieved by using chiral Brønsted acids like binol-derived phosphoric acids or imidodiphosphates in combination with peroxide compounds like hydrogen peroxide or alkylhydroperoxide.

BRIEF DESCRIPTION OF THE DRAWING

The invention will now be described with reference to the drawing, wherein:

FIG. 1 is a schematic showing activation of the peroxide moiety by chiral Brønsted acids.

The inventors found out that peroxide moiety could be activated by bifunctional chiral Brønsted acids through formation of two hydrogen bonds as shown in FIG. 1.

The present invention is therefore directed to a process for preparing sulfoxides by enantioselectively oxidizing thiocompounds with hydrogen peroxide or alkyl hydroperoxide in the presence of a Brønsted acid catalyst, such as chiral imidodiphosphates or phosphoric acids, for example, a binol-derived phosphoric acid, as represented in the following reaction scheme:

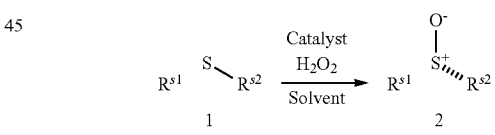

In a broader scope, the invention is directed to oxidizing a compound $X^sR^X_n$ with a peroxide compound ROOH in the presence of a chiral imidodiphosphate catalyst having the general formula (I) below to obtain $X^s(\!-\!\!-\!\!O)R^X_n$— including the representations of $R^x_n X^{s+}\!-\!\!O^-$ and $R^x_n X^s\!=\!\!O\!-\!\!$ and $R^pOH$,

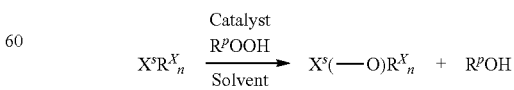

wherein:
  $X^s$ can be selected from S, Se, P or N,
  $R^X$ can be the same or different on X and may be selected from $-NR^Y_2$, $-SR^Y$, $-OR^Y$, $-OSiR^Y_3$, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or heterosubstituents, n is 2 when $X^s$ is S or Se, and n is 3 when $X^s$ is P or N, $R^p$ and $R^Y$ may be independently selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or heterosubstituents, In principle $X^sR^X_n$ can be any S, Se, P or N compound which can be oxidized to give an $S^+$—$O^-$, $Se^+$—$O^-$, $P^+$—$O^-$ or $N^+$—$O^-$ compound as a final product or as an intermediate which is further reacted in the reaction.

In the simplest form, the peroxide compound is hydrogen peroxide, but aliphatic or aromatic hydroperoxides, aliphatic or aromatic percarboxylic acids or mixtures thereof might be used as well.

In a further embodiment, the present invention is directed to a process for oxidizing an alkylene compound to an epoxy compound and optionally, further hydrolyzing said epoxy compound to a hydroxyl compound or, depending on the substituent on the alkylene unit, to an alpha-hydroxy-carbonyl-compound.

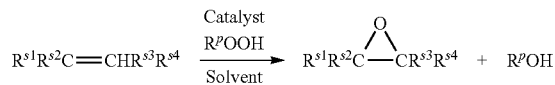

In said reaction scheme, $R^{s1}$ to $R^{s4}$ may have the meaning as given before for $R^X$. In principle any double bond which can be oxidized to give an epoxide, as a final product or as an intermediate which is further reacted in the reaction.

In a still further embodiment, the present invention is directed to a process for oxidizing an alpha-hydrogen-carbonyl-compound to an alpha-hydroxy-carbonyl-compound.

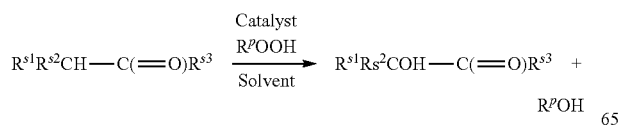

In said reaction scheme, $R^{s1}$ to $R^{s3}$ may have the meaning as given before for $R^X$ and $R^p$ may have the meaning as given before. In principle any alpha-hydrogen-carbonyl-compound which can be oxidized to give an alpha-hydroxy-carbonyl-compound, as a final product or as an intermediate which is further reacted in the reaction. In addition (CO)$R^{s3}$ could be replaced by another electron-withdrawing groups having a tautomerizable double bond adjacent to the CH-site, such as —$NO_2$, —CN.

In embodiments of the inventive processes, the present invention makes use of chiral imidodiphosphates and derivatives thereof having the general formula (I), which have been described in EP12150663.8, as follows:

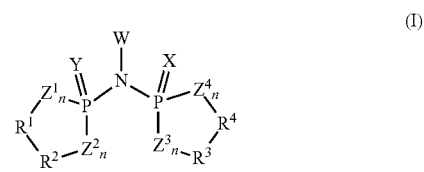

wherein:

X and Y may be, independently from each other, the same or different and represent O, S, Se and $NR^N$, $Z^1$ to $Z^4$ may be, independently from each other, the same or different and represent O, S and $NR^N$, n stands for 0 or preferably 1, W may be substituent being capable of forming a covalent or ionic bond with the imidodiphosphate moiety, $R^1$ to $R^4$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups whereby $R^1$ and $R^2$ are forming a ring system with $Z^1$ and $Z^2$ and $R^3$ and $R^4$ are forming a ring system with $Z^3$ and $Z^4$, respectively, and $R^N$ may be selected from hydrogen, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or heterosubstituents, including its tautomeric and ionic forms, and derivatives thereof.

In the following, it is to be understood that the above formula (I) comprises its tautomeric forms as represented by the formulae (Ia) or (Ib)

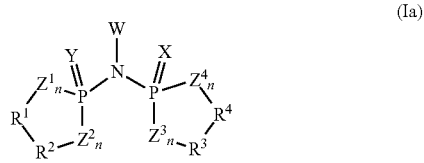

-continued

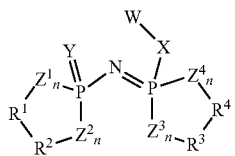
(Ib)

wherein X, Y, $Z^1$ to $Z^4$, n, W, $R^1$ to $R^4$ and $R^N$ have the meaning as defined above. In the following, it is to be understood that any of the formulae (II), (III), (IV) and (V) below comprises its respective tautomeric forms as represented by formula (Ia) or formula (Ib).

In the present application, the expression "imidodiphosphates" is to be understood to comprise derivatives thereof, wherein one or more of the oxygen atoms of the imidodiphosphate moiety is replaced by S, Se, $NR^N$ as defined above.

In the above formula (I) and the derived formulae below, it is to be understood that any tautomeric form of the inventive chiral imidodiphosphates as well as any charged form thereof including any anionic form is to be comprised by the representation of said formula. It is also to be understood that imidodiphosphates could possess inherent chirality even if all of the groups $R^1$ to $R^4$ are achiral groups.

In the above formulae (I), $R^1$ to $R^4$ may be selected each from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or heterosubstituents.

In the above formula (I), W is a substituent being capable of forming a covalent or ionic bond with the imidodiphosphate moiety such as hydrogen, —OH, halogen, a metal such as Li, Na, K, Rb, Cs, Be, Mg, Ca, Sr, Ba, Sc, Ti, V, Cr, Mn, Fe, Co, Ni, Cu, Zn, Y, Zr, Mo, Ru, Rh, Pd, Ag, W, Re, Os, Ir, Pt, Au, Al, Pb, La, Sm, Eu, Yb, U, or a cationic organic group as exemplified in Scheme 2 below, $R^w$ or a substituted silicon such as —$SiR^IR^{II}R^{III}$, wherein $R^w$, $R^I$, $R^{II}$ and $R^{III}$ may be same or different and each stand for hydrogen, halogen, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or a heterosubstituent.

The expression "partially arene-hydrogenated forms thereof" is to be understood that in case that the aromatic structure comprises more than one aromatic cycle such as for naphthalene, at least one aromatic cycle, one aromatic cycle remaining, might be partially or fully hydrogenated.

The anionic form may be complemented by any cation for forming an ion pair.

In one embodiment of the above formulae (I), $Z^1$ to $Z^4$ represent O, n is 1 and the other definitions are as given before for formula (I), as represented by formula (II):

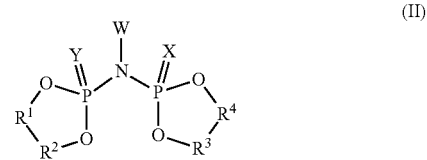
(II)

In such formulae (I) and (II), the moiety

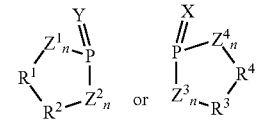

might be a five to ten-membered ring structure of ($R^1$, $R^2$, $Z^1$, $Z^2$ and —PY—) or ($R^3$, $R^4$, $Z^3$, $Z^4$ and —PX—), respectively.

In one embodiment of the compounds of formula (II), X and Y represent O and the other definitions are as given before for formulae (I), as represented by formula (III):

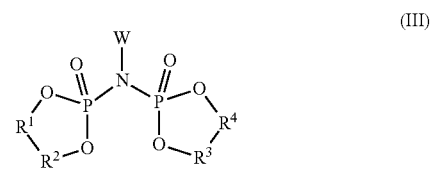
(III)

In such formula (III), at least one of ($R^1$ and $R^2$) and ($R^3$ and $R^4$) may form a ring structure derived from a bridged aromatic structure such as biphenyl optionally substituted, BINOL, TADDOL, VAPOL, SPINOL, 1,1'-binaphthalene, 1,1'-bianthracene, 1,1-biphenanthrene, as well as the partially arene-hydrogenated forms such as 8H-BINOL, each of said rings systems optionally being substituted by one or more substituents selected from heterosubstituents, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon such as aryl, aryl-($C_1$-$C_6$)-alkyl, heteroaryl-($C_1$-$C_6$)-alkyl, each hydrocarbon optionally being substituted by one or more heterosubstituents. In such formula (III), the ring structure formed by ($R^1$ and $R^2$) or ($R^3$ and $R^4$) may be the same or different.

Examples of said compound having the formula (III) and prepared by the inventors are shown below:

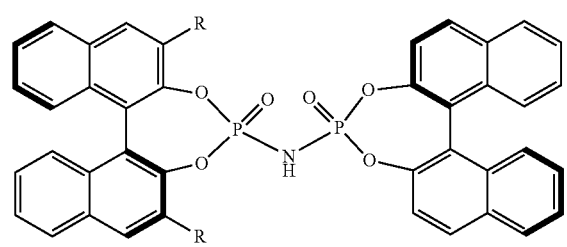

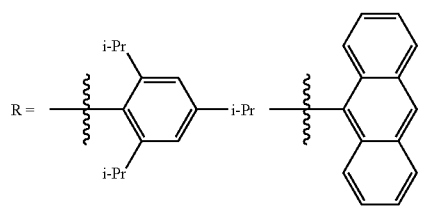

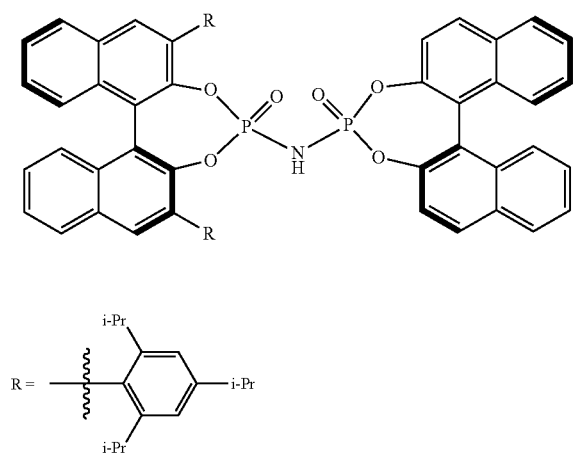

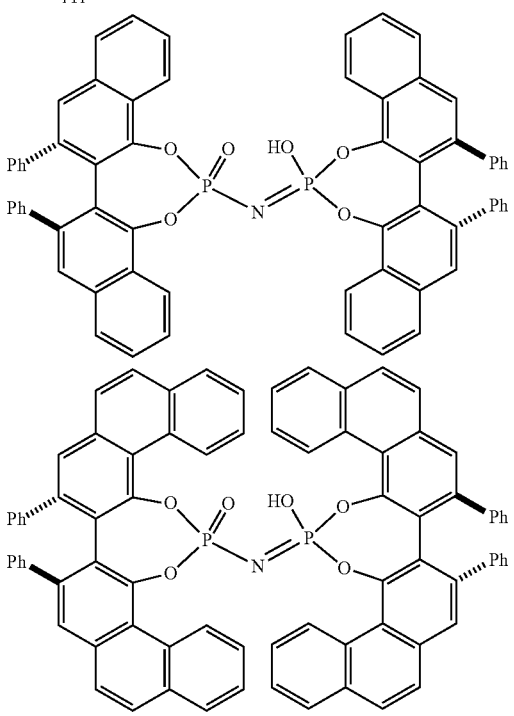

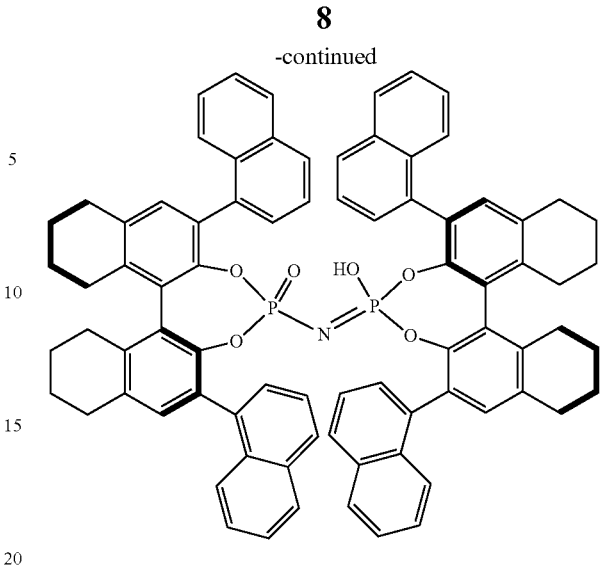

In a further embodiment, the compounds of formula (I) may be represented by formula (IV):

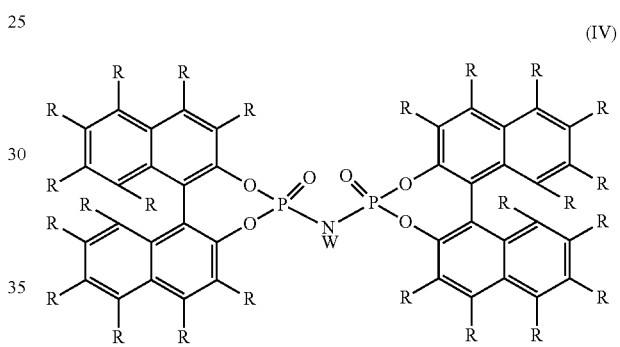

(IV)

In said formula (IV), the substituent R may be the same or different on each position and may each stand for hydrogen, a heterosubstituent, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or a heterosubstituent.

In said formula (IV), W is defined as given before for formula (I).

The substituents on the ring structure proximal to the —Z—P— bond, such as the —O—P-bond, are preferably bulky groups and may be selected from the definitions for $R^N$ or heterosubstituents.

In the inventive processes, the chiral imidodiphosphates having the general formula (II), (III) or (IV) are preferably used.

Basically, any chiral groups are possible as chiral groups for the inventive compounds. If the other group in each case is not chiral, the groups $R^1$ to $R^4$ are any organic group which may be saturated or unsaturated, linear, cyclic or heterocyclic, aromatic and/or heteroaromatic.

Examples of said compound having the formula (IV) and prepared by the inventors are shown below:

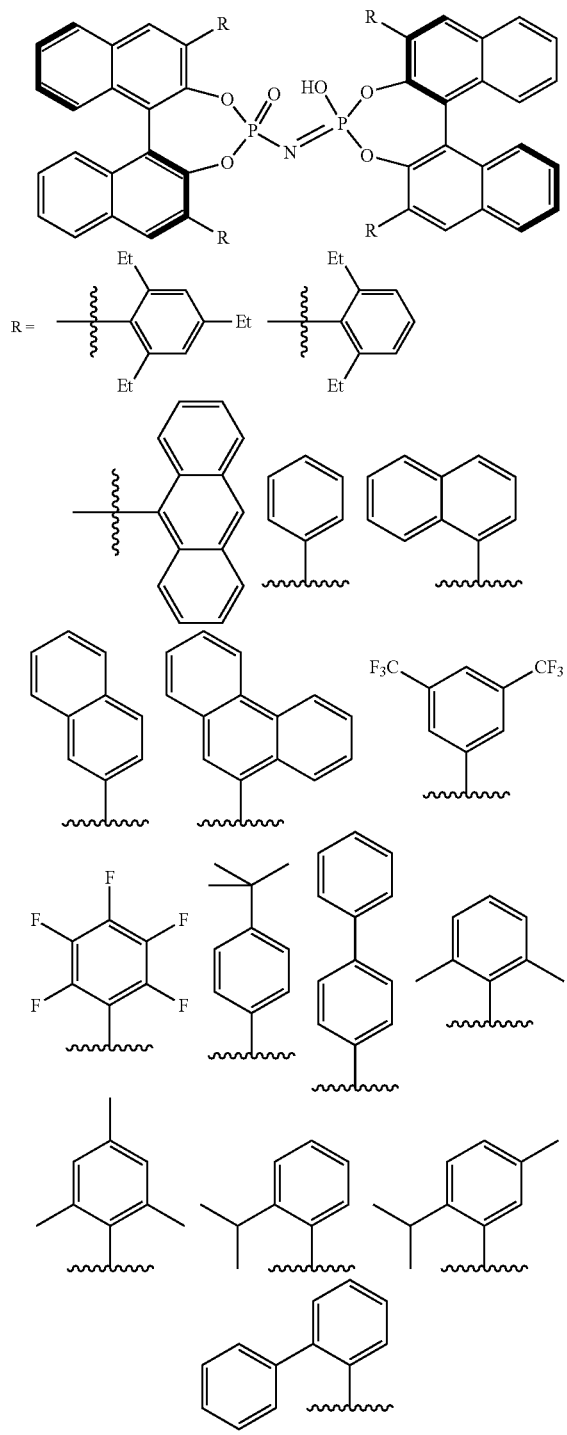

In organic synthesis, particularly in the synthesis of pharmaceutical active compounds, chiral compounds are frequently used as catalysts in order to obtain the desired product in a high enantiomeric purity or diastereomeric purity.

It has been found that the compounds according to the invention are well suited as catalysts for enantioselective synthesis. Here, they function as chiral Brønsted acids or the conjugated bases thereof as chiral anions in enantioselective catalyses directed by counterions.

The following definitions for the individual substituents/groups apply equally as follows.

A heterosubstituent as defined according to the invention can be selected from OH, F, Cl, Br, I, CN, $NO_2$, $SO_3H$, a monohalogenomethyl group, a dihalogenomethyl group, a trihalogenomethyl group, $CF(CF_3)_2$, $SF_5$, amine bound through N atom, —O-alkyl (alkoxy), —O-aryl, —O—$SiR^S_3$, —S—$R^S$, —S(O)—$R^S$, —S(O)$_2$—$R^S$, —COOH, $CO_2$—$R^S$, -amide, bound through C or N atom, formyl group, C(O)—$R^S$, COOM, where M may be a metal such as Na or K. $R^S_3$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups.

Aliphatic hydrocarbons including alkyl, alkenyl and alkinyl may comprise straight-chain, branched and cyclic hydrocarbons.

Heteroaliphatic is a hydrocarbon including alkyl, alkenyl and alkinyl which may comprise straight-chain, branched and cyclic hydrocarbons with one or more carbon atoms substituted with a heteroatom.

In more detail, $C_1$-$C_{20}$-Alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might be cyclopropyl, cyclobutyl, cyclopentyl, cyclohexyl or cycloheptyl. Alkenyl might be $C_2$-$C_{20}$ alkenyl. Alkinyl might be $C_2$-$C_{20}$ alkinyl.

Said unsaturated alkenyl- or alkinyl groups can be used for linking the inventive compounds to a carrier such as a polymer to serve for an immobilized catalyst.

Halogen is F, Cl, Br or I.

Alkoxy is preferably $C_2$-$C_{10}$ alkoxy such as methoxy, ethoxy, propoxy, tert-butoxy etc.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Aryl might be phenyl, naphthyl or biphenyl.

Arylalkyl might be benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothia-zolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3, 4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

In a preferred embodiment of the present invention as for example shown in formula (IV), at least one of R proximal to the —O—P— bond is not hydrogen and may be selected from among methyl, ethyl, isopropyl, cyclohexyl, cyclopentyl, phenyl, 2,4,6-triisopropylphenyl, 2,4,6-triethylphenyl, 2,6-diethylphenyl, 2,6-diethylphenyl, 2-isopropylphenyl, 5-methyl-2-isopropylphenyl, mesityl, 9-phenanthryl, 9-anthracenyl, ferrocenyl, N-(perfluorophenyl)acetamide, N-(4-chlorophenyl)acetamide, N-(naphthalen-1-yl)acetamide, N-benzhydrylacetamide, N-(2,6-diisopropylphenyl)acetamide, 1-anthracenyl, corannulene, porphyrin, 1-naphthyl, 2-naphthyl, 4-biphenyl, 3,5-(trifluoromethyl)phenyl, 2,6-dimethylphenyl, tert-butyl, tris-methylsilyl, tert-butydimethylsilyl, phenyldimethylsilyl, methyldiphenylsilyl, tris-mesitylsilyl, tris-phenylsilyl, 4-nitrophenyl and 2,6-methyl-4-butylphenyl, trifluoromethyl, unbranched (linear) and branched ($C_1$-$C_{12}$)-perfluoroalkyls, 3,4,5-trifluorophenyl, 1,3-bis(perfluoropropan-2-yl)phenyl, 1,3-bis(perfluorobutyl)phenyl and/or pentafluorophenyl and also chloride, iodide, fluoride, COOH, $B(OH)_2$, $B(alkyl)_2$, $B(O-alkyl)_2$, B(pinacol), $BF_3X$ where X=Na or K, OTf. The other groups are preferably hydrogen.

The compounds according to the invention can be converted in process steps which are well known per se to those skilled in the art into organic salts, metal salts or metal complexes. In one possible embodiment, the imidodiphosphates are reacted with an appropriate metal salt, for example with the carbonate of the appropriate metal. Examples of organic salts, metal salts and metal complexes are shown in the following Scheme 1 for formula (V):

Scheme 1: General examples of metal salts and metal complexes of the imidodiphosphates V.

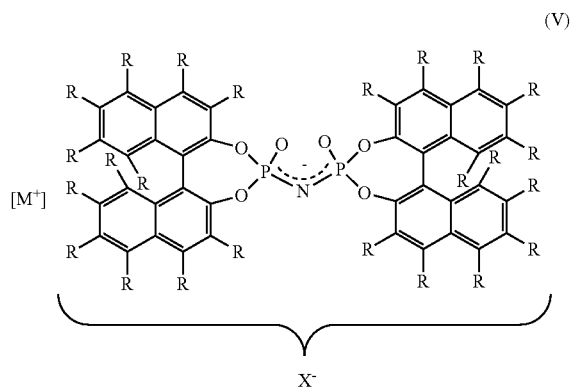

In Scheme 1, any metals or organic cations, e.g. tertiary ammonium ions, can be represented by M. Even though the compounds are shown as salts in scheme 1, the precise structure with metals is not known; they can also have the structure of metal complexes. The formulation metal salts or metal complexes is therefore used for the purposes of the present invention. The metal compounds are not restricted to particular metal compounds or complexes. Suitable metal compounds are derived from Li, Na, K, Rb, Cs, Be, Mg, Ca, Sr, Ba, Sc, Ti, V, Cr, Mn, Fe, Co, Ni, Cu, Zn, Y, Zr, Mo, Ru, Rh, Pd, Ag, W, Re, Os, Ir, Pt, Au, Al, Pb, La, Sm, Eu, Yb, U.

Scheme 2: Examples of possible cations $M^+X^-$

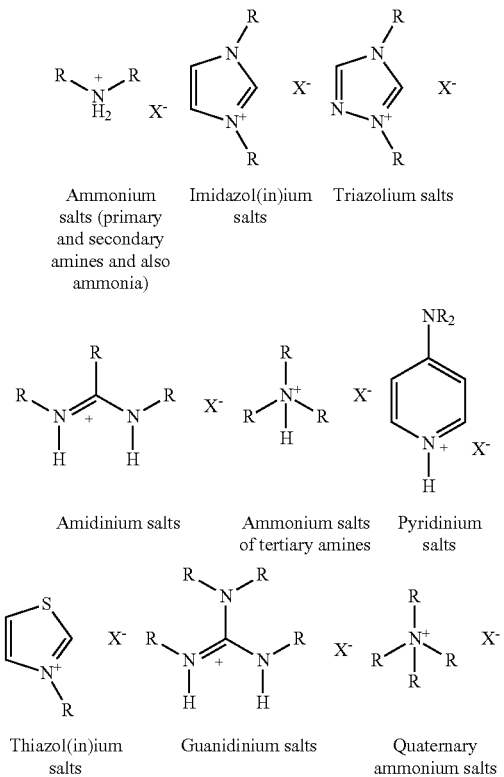

Ammonium salts (primary and secondary amines and also ammonia)   Imidazol(in)ium salts   Triazolium salts Amidinium salts   Ammonium salts of tertiary amines   Pyridinium salts Thiazol(in)ium salts   Guanidinium salts   Quaternary ammonium salts

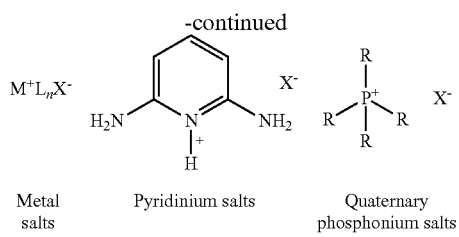

| Metal salts | Pyridinium salts | Quaternary phosphonium salts |

In other embodiments of the inventive processes, the present invention makes use of chiral acids and derivatives thereof as catalysts which are known in the state of art such as those disclosed in:

EP 1623971.
Hoffmann, S., Seayad, A. M. & List, B. Angew. Chem. Int. Ed. 44, 7424-7427 (2005).
Xu, F. et al. J. Org. Chem. 75, 8677-8680 (2010).
Ćorić, I., Müller, S. & List, B. J. Am. Chem. Soc. 132, 17370-17373 (2010).
Nakashima, D. & Yamamoto, H. J. Am. Chem. Soc. 128, 9626-9627 (2006).
Akiyama, T., Itoh, J., Yokota, K. & Fuchibe, K. Angew. Chem. Int. Ed. 43, 1566-1568 (2004).
Uraguchi, D. & Terada, M. J. Am. Chem. Soc. 126, 5356-5357 (2004).
Storer, R. I., Carrera, D. E., Ni, Y. & MacMillan, D. W. C. J. Am. Chem. Soc. 128, 84-86 (2006).
Rowland, G. B. et al. J. Am. Chem. Soc. 127, 15696-15697 (2005).
Akiyama, T., Saitoh, Y., Morita, H. & Fuchibe, K. Adv. Synth. Catal. 347, 1523-1526 (2005).
Müller, S., Webber, M. J. & List, B. J. Am. Chem. Soc., 133, 18534-18537 (2011).
García-García, P., Lay, F., García-García, P., Rabalakos, C. & List, B. Angew. Chem. Int. Ed. 48, 4363-4366 (2009).
Vellalath, S., Ćorić, I. & List, B. Angew. Chem. Int. Ed. 49, 9749-9752 (2010).

Such chiral acid catalyst to be used for the asymmetric oxidation without the need of an intermediate activation reaction making use of an activation reagent such as a coupling agent like carbodiimide here can be selected from chiral phosphoric acids, sulfonic acids, carboxylic acids, bisulfonimides, triflyl phosphoramides, phosphinyl phosphoramides and derivatives thereof preferably on the basis of a aromatic structure as exemplified above for formula (III) such as BINOL, TADDOL, VAPOL, SPINOL, as well as the partially arene-hydrogenated forms thereof such as 8H-BINOL, and comprises a reactive site represented by a formula [—(P,S,C)=O][(—NHR$^E$, —OH]— wherein R$^E$ has the meaning of an electron-withdrawing group, as represented exemplarily as follows:

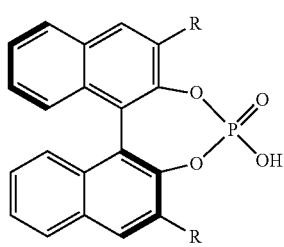

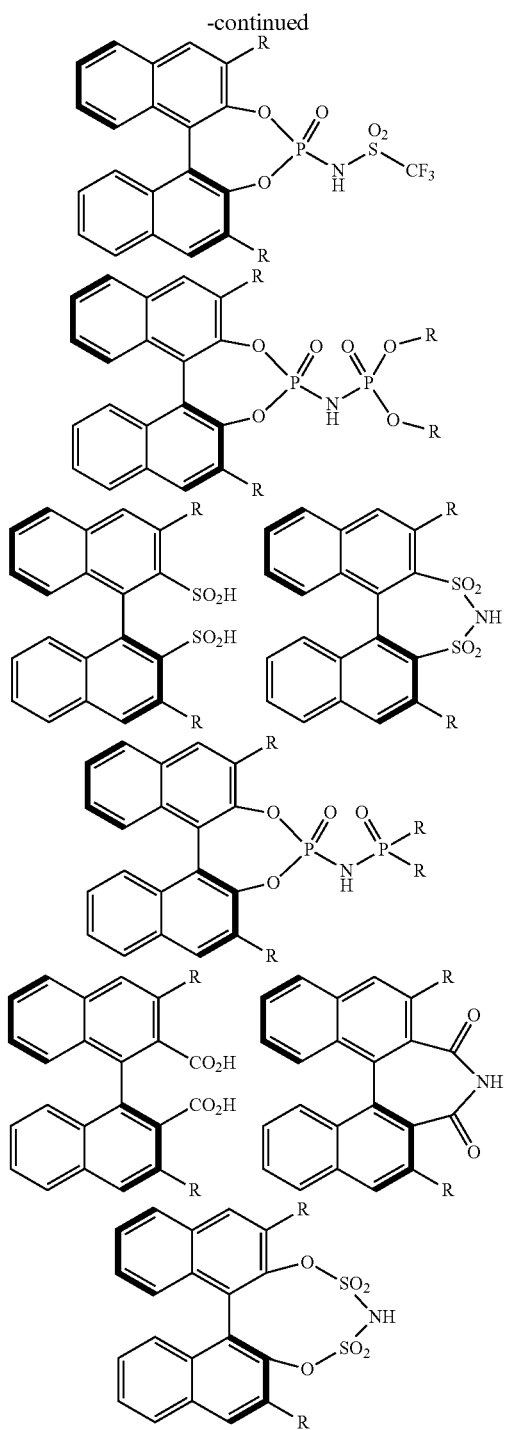

In said formulae, R can have the meaning as given above for R in formula (IV) and its preferred embodiments.

The inventive process is usually carried out in conventional organic solvent such as hydrocarbon solvents such as hexanes, pentane, methylcyclohexane, heptane, isooctane preferably cyclohexane, halogenated solvents such as chloroform, dichloromethane, dichloroethane, chlorobenzene, fluorobenzene, preferably carbon tetrachloride, aromatic solvents such as benzene, toluene, substituted benzenes, xylenes, ethers such as tetrahydrofuran, methyltetrahydrofuran, tert-butylmethyl ether, diisopropyl ether, diethyl ether, dioxane, esters such as ethyl acetate, isopropyl acetate, or any other solvent or mixtures thereof that do not negatively influence the reaction, The inventive process can be carried out under an atmosphere of gas that does not negatively influence the reaction, preferably in a protective atmosphere such as nitrogen, argon, or in air, preferably in a closed container.

The process temperature is usually from −78° C. to 100° C., preferably −20 to 25° C. Addition of a drying agent such as MgSO$_4$, Na$_2$SO$_4$, or molecular sieves to the reaction mixture to partially remove water, is not necessary but can have beneficial effect on the reaction rate, enabling lower catalyst loadings, reduced reaction time, and possibly increase in enantioselectivity.

Though each peroxide might be generally used for the inventive oxidation method, the reaction conditions might be optimized by the choice of the peroxide compound, in particular with respect to the reaction rate and enantioselectivity.

The invention is further illustrated by the following Examples.

Experimental Part

In the following Examples, the general method for oxidizing thiocompounds using hydrogen peroxide is carried out in an organic solvent such as hexane or CCl$_4$ in the presence of an exemplary catalyst such as imidodiphosphate catalyst as exemplified for compounds 5a and 5b. The catalyst preparation is carried out in line with the procedure as illustrated in EP12150663.8 in detail.

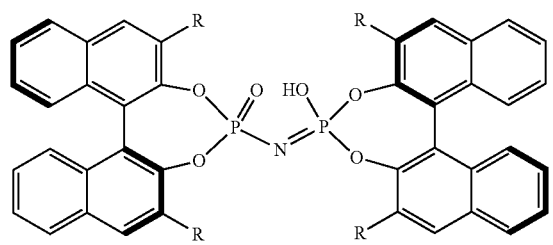

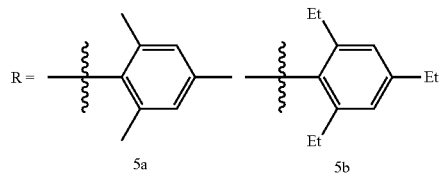

With the addition of MgSO$_4$ to remove water, the reaction time can be significantly shortened to 2 hours, and only 1.05 equivalents of hydrogen peroxides are required (entry 3). Both cyclohexane and CCl$_4$ can be employed as the solvent, giving the same results (entries 3-4). Moreover, the catalyst loading can be lowered to 1 mol %, without erosion of enantioselectivity, though needing a longer reaction time (entry 5). Further lowering the catalyst loading to 0.1 mol % can also give a high enantioselectivity of 95:5 er (entry 6).

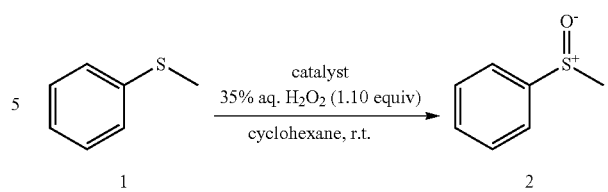

TABLE

Test of bisphosphonimide catalysts.[a]

| Entry | Acid | t (h) | Conversion (%)[b] | Sulfonyl compound (%)[b] | e.r.[c] |
|---|---|---|---|---|---|
| 1 | 5a | 24 | 90 | n.d. | 92:8 |
| 2 | 5b | 24 | 80 | n.d. | 99:1 |
| 3[d] | 5b | 2 | >99 | n.d. | 99:1 |
| 4[d,e] | 5b | 2 | >99 | n.d. | 99:1 |
| 5[d,f] | 5b | 10 | >99 | n.d. | 98.5:1.5 |
| 6[d,g] | 5b | 72 | 75% | n.d. | 95:5 |

[a]0.1 mmol scale, 2 mol % acid, aq. H$_2$O$_2$ (1.10 eq), in cyclohexane (2 mL), r.t.
[b]Determined by GCMS, n.d. = not detected.
[c]Determined by chiral HPLC analysis.
[d]With MgSO$_4$, aq. H$_2$O$_2$ (1.05 eq).
[e]In CCl$_4$.
[f]1 mol % catalyst.
[g]0.1 mol % catalyst.

As it can be seen from the above table, a perfect enantioselectivity was observed with acid 5b. Having the optimized reaction conditions established, the inventors next examined the reaction scope with a series of representative substrates. As revealed in following Table, a remarkable broad range of aryl methyl sulfides can be converted to the corresponding sulfoxides in high yields with excellent enantio- and chemoselectivity, regardless the electronic nature (from —OMe to —NO$_2$) and position (o-, m-, p-) of the substituents. Substrates with a bulky alkyl group can also be oxidized with high enantioselectivity, yet a small amount of sulfone (5-9%) was observed. Remarkably, high yields and optical purity were also obtained in the cases of simple alkyl thioethers. To the best of the inventor's knowledge, the levels of enantioselectivity are the highest so far in organocatalytic systems, and the generality of this novel organocatalytic sulfoxidation is also unprecedented,[8] even when compared to the metal-catalyzed reactions.

TABLE

Substrate scope of asymmetric sulfoxidation.

| Entry | Product (Rs$^1$ and Rs$^2$ as generally defined above and being identifiable from below) | Yield (%)[a] | e.r.[b] |
|---|---|---|---|
| 1 | X = H (2a) | 98 | 99.5:0.5 |

TABLE-continued

Substrate scope of asymmetric sulfoxidation.

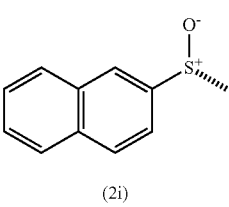

| Entry | Product (Rs¹ and Rs² as generally defined above and being identifiable from below) | Yield (%)[a] | e.r.[b] |
|---|---|---|---|
| 2 | 4-MeO (2b) | 96% | 97.5:2.5 |
| 3 | 4-Me (2c) | 98% | 98:2 |
| 4 | 4-Cl (2d) | 91% | 98.5:1.5 |
| 5 | 3-Cl (2e) | 95% | 99.5:0.5 |
| 6 | 2-Cl (2f) | 99% | 99:1 |
| 7 | 4-CN (2g) | 92% | 97.5:2.5 |
| 8 | 4-NO₂ (2h) | 95% | 99.5:0.5 |
| 9 | (2i) 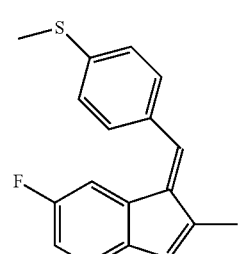 | 98% | 99:1 |
|  | 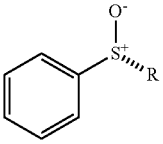 |  |  |
| 10[d] | R = Et (2j) | 90% | 95:5 |
| 11[e] | i-Pr (2k) | 89% | 92.5:7.5 |
| 12[f] | (2l) 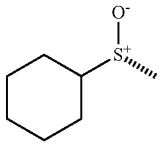 | 96% | 97:3 |
| 13[f,g] | (2m) 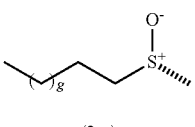 | 96% | 95.5:4.5 |

[a] Isolated yields on 0.1-0.4 mmol scales.
[b] Determined by HPLC analysis on a chiral phase.
[d] 5% sulfone observed by ¹H NMR.
[e] 9% sulfone.
[f] In CCl₄, at 0° C.
[g] 2% sulfone.

The practical synthetic relevance of the inventive method was demonstrated with the enantioselective synthesis of Sulindac, which is an efficient non-steroidal anti-inflammatory drug and recently applied also to the cancer treatment. The oxidation of the Sulindac sulfide was performed under standard reaction conditions, followed by the hydrolysis of the ester group, giving Sulindac in 98% yield and 99:1 er.

Scheme - Enantioselective synthesis of Sulindac.

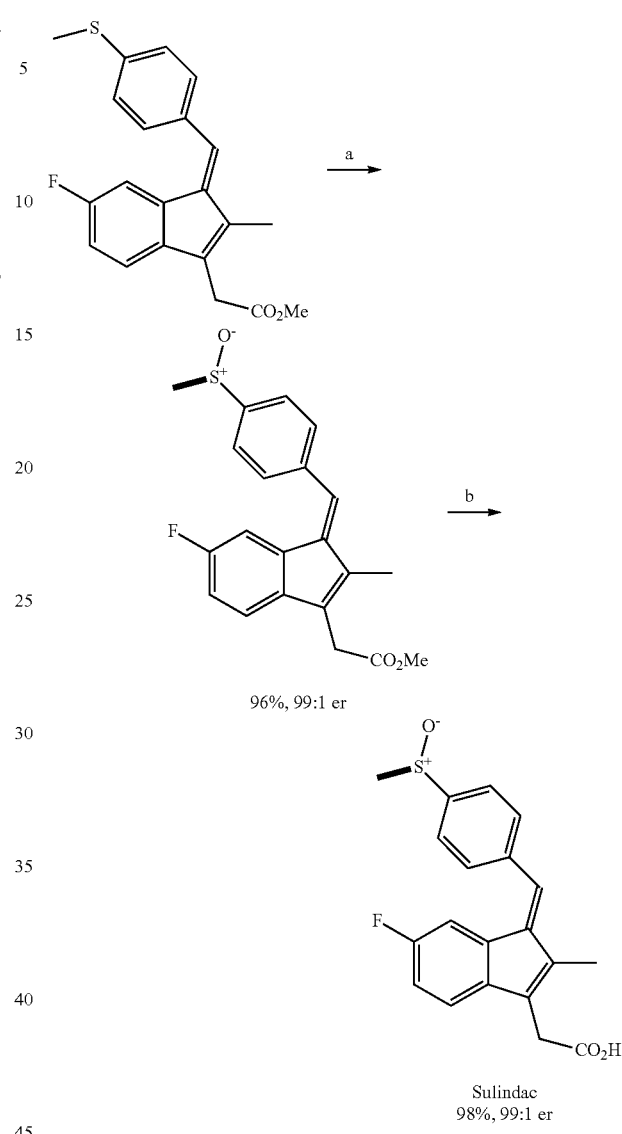

(a) 2 mol % 5b, aq.; H₂O₂, MgSO₄, CCl₄; (b) LiOH, THF/H₂O 5:1

In summary, a novel and highly efficient organocatalytic oxidation system, chiral Brønsted acid/aq. H₂O₂, has been developed, and successfully applied to the sulfoxidation of thioethers with excellent enantioselectivity and chemoselectivity. The observed generality and high levels of enantioselectivity are unprecedented in the area of organocatalytic sulfoxidation reactions.

General Procedure for the Asymmetric Oxidation of Sulfides in the Presence of a Imidodiphosphate Catalyst

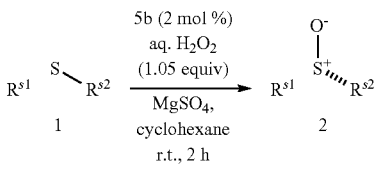

To a solution of phenyl methyl sulfide (24 mg, 24 μL, 0.2 mmol, 1.0 equiv) and the acid catalyst 5b (6 mg, 4.0 μmol, 0.02 equiv) in 2 mL of cyclohexane was added MgSO$_4$ (90 mg) and aq. H$_2$O$_2$ (35%, 18 μL, 0.21 mmol, 1.05 equiv) in one portion. The resulting mixture was stirred vigorously at room temperature until no more conversion was observed by TLC or GCMS (2 h). Purification by column chromatography on silica gel (EtOAc) gave the desired sulfoxide as a white solid. The ratios of sulfoxide/sulfone were determined by $^1$H-NMR analysis of the crude product. The optical purity of the product was determined by HPLC analysis (Daicel Chiralcel OB-H, heptane/isopropanol 70:30, 0.5 ml/min, 254 nm). The absolute configuration of the sulfoxide was determined by comparison of the HPLC retention times and the optical rotation with the literature values.

The following compounds were produced in line with the general procedure as detailed before:

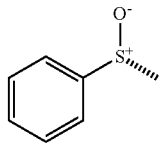

C$_7$H$_8$OS (140.20 g/mol), white solid, purified by column chromatography on silica gel (EtOAc), 98% yield; $^1$H NMR (300 MHz, CDCl$_3$): δ 2.73 (s, 3H, CH$_3$), 7.50-7.55 (m, 3H, ArH), 7.66 (d, J=7.8 Hz, 2H, ArH); $^{13}$C NMR (75 MHz, CDCl$_3$): δ 44.0, 123.5, 129.4, 131.0, 145.7 (d); MS (EI): m/z 140 (M$^+$); HPLC: The optical purity (er=99.5:0.5) was determined by HPLC (DAICEL OB-H, heptane/isopropanol 70:30, flow rate: 0.5 mL/min, 254 nm, t$_r$=13.4 and 21.8 min).

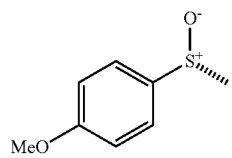

C$_8$H$_{10}$O$_2$S (170.23 g/mol), white solid, purified by column chromatography on silica gel (EtOAc/hexanes, 1:1), 96% yield; $^1$H NMR (500 MHz, CDCl$_3$): δ 2.70 (s, 3H, CH$_3$), 3.86 (s, 3H, OCH$_3$), 7.03 (dt, J=8.8, 2.0 Hz, 2H, ArH), 7.60 (dt, J=8.8, 2.0 Hz, 2H, ArH); $^{13}$C NMR (125 MHz, CDCl$_3$): δ 44.0, 55.5, 114.8, 125.5, 136.6, 162.0; MS (EI): m/z 170 (M$^+$); HPLC: The optical purity (er=97.5:2.5) was determined by HPLC (DAICEL OB-H, heptane/isopropanol 50:50, flow rate: 0.5 mL/min, 254 nm, t$_r$=11.7 and 19.0 min).

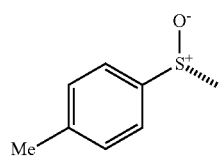

C$_8$H$_{10}$OS (154.23 g/mol), white solid, purified by column chromatography on silica gel (EtOAc/hexanes, 1:1), 98% yield; $^1$H NMR (500 MHz, CDCl$_3$): δ 2.41 (s, 3H, Ar—CH$_3$), 2.71 (s, 3H, CH$_3$), 7.33 (d, J=8.2 Hz, 2H, ArH), 7.54 (d, J=8.2 Hz, 2H, ArH); $^{13}$C NMR (125 MHz, CDCl$_3$): δ 21.4, 44.0, 123.6, 130.1, 141.5, 142.5; MS (EI): m/z 154 (M$^+$); HPLC: The optical purity (er=98:2) was determined by HPLC (DAICEL OB-H, heptane/isopropanol 50:50, flow rate: 0.5 mL/min, 220 nm, t$_r$=9.5 and 15.2 min).

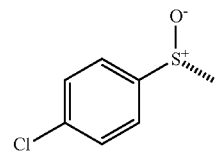

C$_7$H$_7$ClOS (174.65 g/mol); white solid, purified by column chromatography on silica gel (EtOAc), 97% yield; $^1$H NMR (500 MHz, CDCl$_3$): δ 2.73 (s, 3H, CH$_3$), 7.52 (d, J=8.5 Hz, 2H, ArH), 7.60 (d, J=8.5 Hz, 2H, ArH); $^{13}$C NMR (125 MHz, CDCl$_3$): δ 44.0, 125.0, 129.7, 137.3, 144.2; MS (EI): m/z 174 (M$^+$); HPLC: The optical purity (er=98.5:1.5) was determined by HPLC (DAICEL OB-H, heptane/isopropanol 50:50, flow rate: 0.5 mL/min, 254 nm, t$_r$=9.9 and 12.5 min).

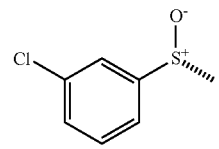

C$_7$H$_7$ClOS (174.65 g/mol); white solid, purified by column chromatography on silica gel (EtOAc), 95% yield; $^1$H NMR (500 MHz, CDCl$_3$): δ 2.75 (s, 3H, CH$_3$), 7.47-7.51 (m, 3H, ArH), 7.67 (d, J=0.8 Hz, 1H, ArH); $^{13}$C NMR (125 MHz, CDCl$_3$): δ 44.0, 121.6, 123.6, 130.6, 131.2, 135.7, 147.8; MS (EI): m/z 174 (M$^+$); HPLC: The optical purity (er=99.5:0.5) was determined by HPLC (DAICEL OB-H, heptane/isopropanol 50:50, flow rate: 0.5 mL/min, 254 nm, t$_r$=10.4 and 12.7 min).

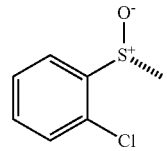

C$_7$H$_7$ClOS (174.65 g/mol); white solid, purified by column chromatography on silica gel (EtOAc/hexanes, 1:1), 99% yield; $^1$H NMR (500 MHz, CDCl$_3$): δ 2.83 (s, 3H, CH$_3$), 7.40 (dd, J=7.9, 1.1 Hz, 1H, ArH), 7.45 (td, J=7.6, 1.4 Hz, 1H, ArH), 7.55 (td, J=7.5, 1.1 Hz, 1H, ArH), 7.96 (dd, J=7.8, 1.4 Hz, 1H, ArH); $^{13}$C NMR (125 MHz, CDCl$_3$): δ 41.8, 125.3, 128.2, 129.8, 132.0, 143.7; MS (EI): m/z 174 (M$^+$); HPLC: The optical purity (er=99:1) was determined by HPLC (DAICEL OB-H, heptane/isopropanol 50:50, flow rate: 0.5 mL/min, 254 nm, t$_r$=10.1 and 14.0 min).

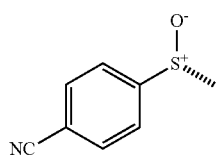

C₈H₇NOS (165.21 g/mol), white solid, purified by column chromatography on silica gel (EtOAc), 92% yield; ¹H NMR (500 MHz, CDCl₃): δ 2.77 (s, 3H, CH₃), 7.78 (dt, J=8.6, 2.0 Hz, 2H, ArH), 7.84 (dt, J=8.6, 2.0 Hz, 2H, ArH); ¹³C NMR (125 MHz, CDCl₃): δ 43.8, 114.8, 117.7, 124.3, 133.0, 151.5; MS (EI): m/z 165 (M⁺); HPLC: The optical purity (er=97.5:2.5) was determined by HPLC (DAICEL OB-H, heptane/isopropanol 50:50, flow rate: 0.5 mL/min, 254 nm, t$_r$=21.5 and 26.7 min).

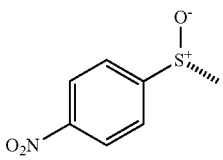

C₇H₇NO₃S (185.20 g/mol), white solid, purified by column chromatography on silica gel (EtOAc), 95% yield; ¹H NMR (500 MHz, CDCl₃): δ 2.80 (s, 3H, CH₃), 7.84 (dt, J=8.7, 1.9 Hz, 2H, ArH), 7.85 (dt, J=8.7, 1.9 Hz, 2H, ArH); ¹³C NMR (125 MHz, CDCl₃): δ 43.9, 124.5, 124.7, 149.5, 153.3; MS (EI): m/z 185 (M⁺); HPLC: The optical purity (er=99.5:0.5) was determined by HPLC (DAICEL OB-H, heptane/isopropanol 50:50, flow rate: 0.5 mL/min, 254 nm, t$_r$=24.7 and 28.4 min).

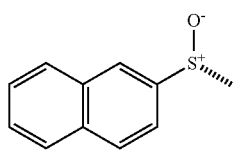

C₁₁H₁₀OS (190.26 g/mol), white solid, purified by column chromatography on silica gel (EtOAc), 98% yield; ¹H NMR (500 MHz, CDCl₃): δ 2.80 (s, 3H, CH₃), 7.59-7.62 (m, 3H, ArH), 7.90-8.00 (m, 3H, ArH), 8.22 (d, J=1.5 Hz, 1H, ArH); ¹³C NMR (125 MHz, CDCl₃): δ 43.8, 119.4, 124.1, 127.4, 127.8, 128.1, 128.5, 129.6, 132.9, 134.4, 142.7; MS (EI): m/z 190 (M⁺); HPLC: The optical purity (er=99:1) was determined by HPLC (DAICEL OB-H, heptane/isopropanol 50:50, flow rate: 0.5 mL/min, 254 nm, t$_r$=11.4 and 14.0 min).

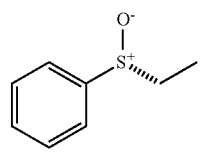

C₈H₁₀OS (154.23 g/mol); white solid, purified by column chromatography on silica gel (EtOAc), 90% yield; ¹H NMR (500 MHz, CDCl₃): δ 1.19 (t, J=7.4 Hz, 3H, CH₃), 2.76 (m, 1H, CH₂), 2.90 (m, 1H, CH₂), 7.47-7.54 (m, 3H, ArH), 7.60-7.62 (m, 2H, ArH); ¹³C NMR (125 MHz, CDCl₃): δ 5.9, 50.2, 124.1, 129.1, 130.9, 143.3; MS (EI): m/z 154 (M⁺); HPLC: The optical purity (er=95:5) was determined by HPLC (DAICEL OB-H, heptane/isopropanol x, flow rate: 0.5 mL/min, 254 nm, t$_r$=9.4 and 14.8 min).

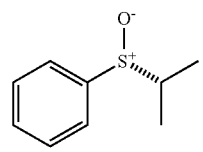

C₉H₁₂OS (168.26 g/mol), colorless oil, purified by column chromatography on silica gel (EtOAc/hexanes, 1:1), 89% yield; ¹H NMR (500 MHz, CDCl₃): δ 1.14 (d, J=6.9 Hz, 3H, CH₃), 1.23 (d, J=6.9 Hz, 3H, CH₃), 2.84 (m, 1H, CH), 7.50 (m, 3H, ArH), 7.60 (m, 2H, ArH); ¹³C NMR (125 MHz, CDCl₃): δ 14.0, 15.9, 54.5, 125.0, 128.9, 131.0, 141.7; MS (EI): m/z 168 (M⁺); HPLC: The optical purity (er=92.5:7.5) was determined by HPLC (DAICEL OB-H, heptane/isopropanol 50:50, flow rate: 0.5 mL/min, 254 nm, t$_r$=8.6 and 11.5 min).

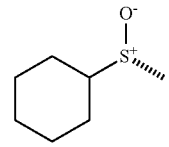

C₇H₁₄OS (146.25 g/mol); white solid, purified by column chromatography on silica gel (EtOAc), 96% yield; ¹H NMR (500 MHz, CDCl₃): δ 1.25-1.46 (m, 5H, CH₂), 1.71-1.74 (m, 1H, CH₂), 1.87-1.95 (m, 3H, CH₂), 2.14-2.17 (m, 1H, CH₂), 2.49-2.55 (m, 4H, SCH₃); ¹³C NMR (125 MHz, CDCl₃): δ 24.9, 25.2, 25.4, 25.5, 26.0, 35.2, 60.9; HPLC: MS (EI): m/z 146 (M⁺); HPLC: The optical purity (er=97:3) was determined by HPLC (DAICEL OB-H, heptane/isopropanol 90:10, flow rate: 0.5 mL/min, 220 nm, t$_r$=8.6 and 11.5 min).

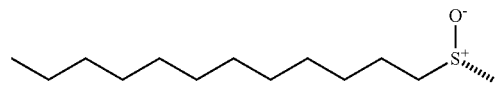

C₁₃H₂₈OS (232.43 g/mol); white solid, purified by column chromatography on silica gel (EtOAc), 96% yield; ¹H NMR (500 MHz, CDCl₃): δ 0.88 (t, J=6.9 Hz, 3H, CH₃), 1.26-1.35 (m, 16H, CH₂), 1.39-1.52 (m, 2H, CH₂), 1.74-1.77 (m, 2H, CH₂), 2.60 (s, 3H, SCH₃), 2.68 (m, 1H, SCH₂), 2.78 (m, 1H, SCH₂); ¹³C NMR (125 MHz, CDCl₃): δ 14.1, 22.6, 22.7, 28.8, 29.19, 29.25, 29.34, 29.36, 29.5, 29.6, 31.9, 38.2, 54.6; MS (EI): m/z 232 (M⁺); HPLC: The optical purity (er=95.5:4.5) was determined by HPLC (DAICEL OB-H, heptane/isopropanol 98:2, flow rate: 0.5 mL/min, 220 nm, t$_r$=20.4 and 22.7 min).

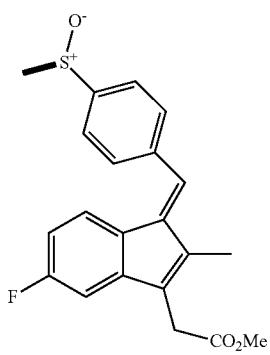 [SMILES: COC(=O)CC1=C(C)/C(=C/c2ccc([S@@+](C)[O-])cc2)c2ccc(F)cc21]

Sulindac methyl ester, $C_{21}H_{19}FO_3S$ (370.44 g/mol); white solid, purified by column chromatography on silica gel (EtOAc), 96% yield; $^1$H NMR (500 MHz, CDCl$_3$): δ 2.13 (s, 3H, CH$_3$), 2.73 (s, 3H, CH$_3$), 3.49 (s, 2H, CH$_2$), 3.63 (s, 3H, CH$_3$), 6.48 (dt, J=8.5 and 2.0 Hz, 1H, CH), 6.80 (dd, J=8.5 and 2.0 Hz, 1H, 7.06-7.08 (m, 2H, 7.59 (d, J=8.0 Hz, 2H, 7.64 (d, J=8.0 Hz, 2H, CH); $^{13}$C NMR (125 MHz, CDCl$_3$): δ 10.4, 31.5, 43.8, 52.2, 106.1, 110.7, 123.6, 123.7, 128.1, 129.4, 130.2, 131.7, 138.1, 139.6, 141.5, 145.4, 146.6, 162.3, 164.2, 170.6; MS (EI): m/z 370 (M$^+$); HPLC: The optical purity (er=99:1) was determined by HPLC (DAICEL AD-3, heptane/isopropanol 90:10, flow rate: 1 mL/min, 254 nm, t$_r$=13.1 and 14.2 min).

Asymmetric Oxidation of Sulfides in the Presence of a Phosphate Catalyst

In the following Examples, the inventors describe the use of chiral phosphoric acids, such as (S)-STRIP as catalysts using alkyl hydroperoxides. The inventors have found that the size of the alkyl group on the hydroperoxide oxidant had a positive effect on the enantioselectivity. For substrate in entry 1 in Table below tert-butyl hydroperoxide gave e.r. 87:13, and hydrogen peroxide 58:42.

TABLE

Substrate scope of phosphoric acid catalyzed asymmetric sulfoxidation.

| Entry | Sulfide | Yield | e.r. |
|---|---|---|---|
| 1 | X = H | 93% | 91:9 |
| 2 | 4-MeO | | 93:7 |
| 3 | 4-Me | 92% | 94:6 |
| 4 | 4-Cl | 88% | 93:7 |
| 5 | 3-Cl | 88% | 93:7 |
| 6 | 2-Cl | 88% | 90:10 |
| 7 | 4-NO$_2$ | 95% | 90:10 |
| 8 | R = i-Pr | 92% | 93:7 |
| 9 | R = t-Bu | 88% | 95:5 |

Reaction scope was investigated under the optimized reaction conditions. As shown in the Table above, the substrate scope is quite general, various sulfides, electron-rich or poor can all be converted into desired sulfoxides in high chemical yields and high enantioselectivities. Remarkably, bulky groups are also tolerated quite well, and even higher enantioselectivity was observed with substrates like phenyl tertbutyl sulfide (entry 9). To the best of inventors knowledge, 95:5 er is the best results so far and even enzymes failed to oxidize this difficult substrate with high enantioselectivity.

A synthetic application of this novel organocatalytic method was carried out in the preparation of a Sulindac analogue. Under optimized conditions, sulfide 3 was converted into sulfoxide 4 in 98% yield and 95:5 er.

Scheme 3. Synthesis of a potent inhibitor of histone deacetylases.

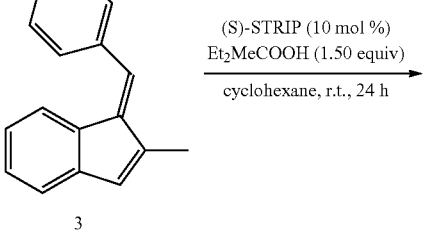

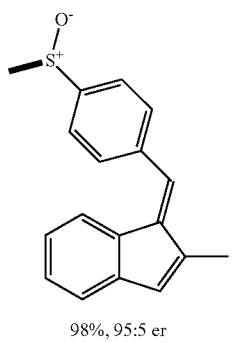

98%, 95:5 er
4

The invention claimed is:

1. A process for the asymmetric oxidation of an organic compound by electrophilic addition of a peroxide compound, said process comprising reacting the organic compound with at least one peroxide compound $R^P$—OOH in the presence of a chiral catalyst;

wherein the at least one peroxide compound is activated in favor of said reacting by hydrogen bonding of the at least one peroxide compound to said chiral catalyst;

wherein said chiral catalyst is selected from the group consisting of chiral compounds (a) and (b), wherein the chiral compounds (a) are selected from the group consisting of chiral imidodiphosphates, and the chiral compounds (b) are selected from the group consisting of phosphoric acids, sulfonic acids, bisulfonimides, triflyl phosphoramides, and phosphinyl phosphoramides, said chiral compounds (b) comprising a catalytically active site [—(P,S)=O][—NHR$^E$, —OH], wherein R$^E$ is an electron-withdrawing group;

wherein the organic compound to be oxidized is selected from the group consisting of $x^s R^X{}_n$, $R^{s1}R^{s2}C=CR^{s3}R^{s4}$ and $R^{s1}R^{s2}CH$—(C=O)$R^{s3}$;

wherein:

$X^s$ is selected from the group consisting of S, Se, P and N;

$R^X$ is the same or different on X and is selected from the group consisting of (a) —NR$^Y{}_2$, (b) —SR$^Y$, (c) —OR$^Y$, (d) —OSiR$^Y{}_3$, (e) $C_1$ to $C_{20}$ straight chain, branched chain or cyclic aliphatic hydrocarbons, optionally having one or more unsaturated bonds, (f) $C_3$-$C_8$-heterocycloalkyl and (g) $C_6$ to $C_{20}$ aromatic hydrocarbon and partially arene-hydrogenated forms, wherein each of (e)-(g) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms;

n is 2 when $X^s$ is S or Se; or n is 3 when $X^s$ is P or N;

$R^P$, $R^Y$ and $R^{s1}$ to $R^{s4}$ are independently selected from the group consisting of (a) $C_1$ to $C_{20}$ straight chain, branched chain or cyclic aliphatic hydrocarbons, optionally having one or more unsaturated bonds, (b) $C_3$-$C_8$-heterocycloalkyl and (c) $C_6$ to $C_{20}$ aromatic hydrocarbon and partially arene-hydrogenated forms, wherein each of (a)-(c) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms; or R' is hydrogen or a radical of the formula:

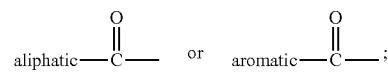

wherein aliphatic or aromatic in said formula is selected from the group consisting of (a) $C_1$ to $C_{20}$ straight chain, branched chain or cyclic aliphatic hydrocarbons, optionally having one or more unsaturated bonds, (b) $C_3$-$C_8$-heterocycloalkyl and (c) $C_6$ to $C_{20}$ aromatic hydrocarbon and partially arene-hydrogenated forms, wherein each of (a)-(c) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms;

wherein said imidodiphosphates have the formula (I):

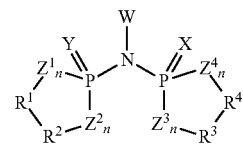

(I)

wherein:

X and Y are, independently from each other, the same or different and represent O, S, Se or NR$^N$;

$Z^1$ to $Z^4$ are, independently from each other, the same or different and represent O, S or NR$^N$;

n stands for 0 or 1;

W is a substituent being capable of forming a covalent or ionic bond with the imidodiphosphate moiety;

$R^1$ to $R^4$ are, independently from each other, the same or different and are each selected from the group consisting of aliphatic, heteroaliphatic, aromatic and heteroaromatic groups, each of which groups is optionally further substituted by one or more metal-free heterosubstituents, aliphatic, heteroaliphatic, aromatic or heteroaromatic groups, whereby $R^1$ and $R^2$ form a ring system with P and, if present, $Z^1$ and $Z^2$, and $R^3$ and $R^4$ form a ring system with P and, if present, $Z^3$ and $Z^4$, respectively; and $R^N$ is selected from the group consisting of (a) hydrogen, (b) $C_1$ to $C_{20}$ straight chain, branched chain or cyclic aliphatic hydrocarbons, optionally having one or more unsaturated bonds, (c) $C_3$-$C_8$-heterocycloalkyl and (d) $C_6$ to $C_{20}$ aromatic hydrocarbon and partially arene-hydrogenated forms, wherein each of (b)-(d) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms;

and tautomeric and ionic forms of said imidodiphosphates.

2. The process according to claim 1, wherein the imidodiphosphate of formula (I) is represented by formula (IV):

(IV)

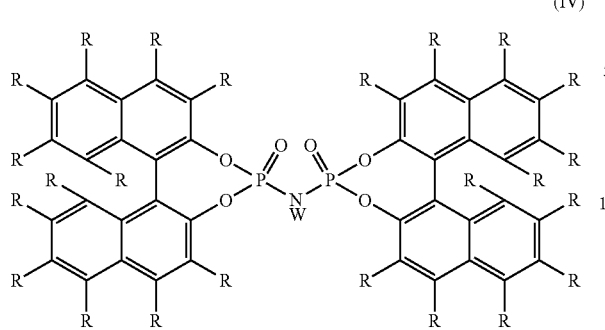

wherein in said formula (IV), the substituent R is the same or different on each position and is a metal-free heterosubstituent or $R^N$.

3. The process according to claim 2, wherein the chiral imidodiphosphate of formula (IV) has the following formula (IVa):

(IVa)

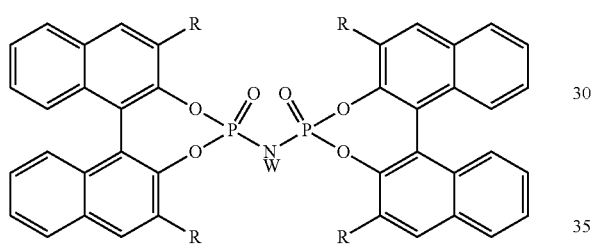

wherein the substituents R are different or optionally the same on each position, or its tautomeric or ionic form.

4. The process according to claim 1, wherein the chiral catalyst used is the chiral imidodiphosphate, and the chiral imidodiphosphate has the formula (II):

(II)

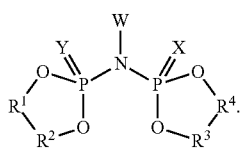

5. The process according to claim 4, wherein the chiral imidodiphosphate of formula (II) has at least one moiety:

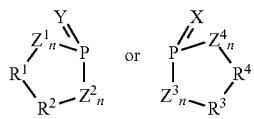

that is a five to ten-membered ring structure.

6. The process according to claim 4, wherein the chiral catalyst used is the chiral imidodiphosphate, and the chiral imidodiphosphate has the formula (III):

(III)

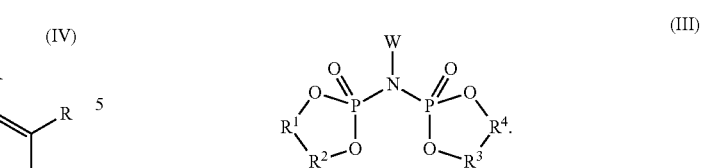

7. The process according to claim 6, wherein, in such formula (III), $R^1$ to $R^4$, respectively are each selected from the group consisting of (a) $C_1$ to $C_{20}$ straight chain, branched chain or cyclic aliphatic hydrocarbons, optionally having one or more unsaturated bonds, (b) $C_3$-$C_8$-heterocycloalkyl and (c) $C_6$ to $C_{20}$ aromatic hydrocarbon and partially arene-hydrogenated forms, wherein each of (a)-(c) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl and (iii) $C_6$ to $C_{20}$ aromatic hydrocarbon and partially arene-hydrogenated forms; and W is selected from the group consisting of (a) hydrogen, (b) —OH, (c) halogen, (d) a metal, (e) a cationic organic group, (f) $R^w$ and (g) a substituted silicon —$SiR^I R^{II} R^{III}$, wherein $R^w$, $R^I$, $R^{II}$ and $R^{III}$ are the same or different and each is selected from the group consisting of (i) hydrogen, (ii) halogen, (iii) $C_1$ to $C_{20}$ straight chain, branched chain or cyclic aliphatic hydrocarbons, optionally having one or more unsaturated bonds, (iv) $C_3$-$C_8$-heterocycloalkyl and (v) $C_6$ to $C_{20}$ aromatic hydrocarbon and partially arene-hydrogenated forms, wherein each of (iii)-(v) is optionally substituted by one or more groups selected from the group consisting of (1) $C_1$ to $C_{20}$ straight chain, branched chain or cyclic aliphatic hydrocarbons, optionally having one or more unsaturated bonds, (2) $C_3$-$C_8$-heterocycloalkyl and (3) $C_6$ to $C_{20}$ aromatic hydrocarbon and partially arene-hydrogenated forms thereof;

and its tautomeric and ionic forms.

8. The process according to claim 6, wherein, in such formula (III), ($R^1$ and $R^2$) and ($R^3$ and $R^4$), respectively each form a ring structure which is the same or different and is derived from a bridged, optionally dimeric, aromatic structure, or a partially arene-hydrogenated form of such aromatic ring structure, each of said rings systems optionally being substituted by one or more substituents which are the same or different on each position and are each selected from the group consisting of (a) hydrogen, (b) metal-free heterosubstituents, (c) $C_1$ to $C_{20}$ straight chain, branched chain or cyclic aliphatic hydrocarbons, optionally having one or more unsaturated bonds, (d) $C_3$-$C_8$-heterocycloalkyl and (e) $C_6$ to $C_{20}$ aromatic hydrocarbon and partially arene-hydrogenated forms, wherein each of (c)-(e) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl and (iii) $C_6$ to $C_{20}$ aromatic hydrocarbon and partially arene-hydrogenated forms;

and its tautomeric and ionic forms.

9. The process according to claim 1, wherein at least one of said ring structures formed by ($R^1$ and $R^2$) or ($R^3$ and $R^4$) is chiral, optionally with a $C_2$ symmetry axis.

10. The process according to claim 1, wherein the ring structures formed by ($R^1$ and $R^2$) and ($R^3$ and $R^4$), respectively, are identical.

11. The process according to claim 1, wherein the organic compound is enantioselectively oxidized with a peroxide compound in the presence of a chiral imidodiphosphate catalyst, said imidodiphosphate having the formula (I).

12. The process according to claim 1, wherein, in the formula (I), W represents hydrogen.

13. The process according to claim 1, wherein the organic compound has the formula $X^S R^X_n$, wherein $X^S$ represents S; n represents 2; and $R^X$ is selected from the group consisting of (a) $C_1$ to $C_{20}$ straight chain, branched chain or cyclic aliphatic hydrocarbons, optionally having one or more unsaturated bonds, (b) $C_3$-$C_8$-heterocycloalkyl and (c) $C_6$ to $C_{20}$ aromatic hydrocarbon and partially arene-hydrogenated forms, wherein each of (a)-(c) is optionally substituted by one or more groups selected from (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms.

14. The process according to claim 1, wherein the peroxide $R^P$—OOH is selected from the group consisting of (a) hydrogen peroxide, (b) aliphatic or aromatic hydroperoxide, (c) aliphatic or aromatic percarboxylic acid and (d) mixtures thereof.

15. A process for the asymmetric oxidation of an organic compound, said process comprising reacting the organic compound with at least one peroxide compound $R^P$—OOH in the presence of a chiral catalyst;
wherein the at least one peroxide compound is activated in favor of said reacting by hydrogen bonding of the at least one peroxide compound to said chiral catalyst;
wherein said organic compound is selected from the group consisting of organic compounds of the formulae $X^S R^X_n$, $R^{s1}R^{s2}C=CR^{s3}R^{s4}$ and $R^{s1}R^{s2}CH—(C=O)R^{s3}$;
wherein:
$X^S$ is selected from the group consisting of S, Se, P and N;
$R^X$ is the same or different on X and is selected from the group consisting of (a) —$NR^Y_2$, (b) —$SR^Y$, (c) —$OR^Y$, (d) —$OSiR^Y_3$, (e) $C_1$ to $C_{20}$ straight chain, branched chain or cyclic aliphatic hydrocarbons, optionally having one or more unsaturated bonds, (f) $C_3$-$C_8$-heterocycloalkyl and (g) $C_6$ to $C_{20}$ aromatic hydrocarbon and partially arene-hydrogenated forms, wherein each of (e)-(g) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms;
n is 2 when $X^S$ is S or Se; or n is 3 when $X^S$ is P or N;
$R^P$, $R^Y$ and $R^{s1}$ to $R^{s4}$ are independently selected from the group consisting of (a) $C_1$ to $C_{20}$ straight chain, branched chain or cyclic aliphatic hydrocarbons, optionally having one or more unsaturated bonds, (b) $C_3$-$C_8$-heterocycloalkyl and (c) $C_6$ to $C_{20}$ aromatic hydrocarbon and partially arene-hydrogenated forms, wherein each of (a)-(c) is optionally substituted by one or more groups selected from the group consisting of (i) $C_1$ to $C_{20}$ straight chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms; or $R^P$ is hydrogen or a radical of the formula:

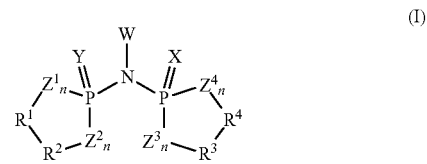

wherein aliphatic or aromatic in said formula is selected from the group consisting of (a) $C_1$ to $C_{20}$ straight chain, branched chain or cyclic aliphatic hydrocarbons, optionally having one or more unsaturated bonds, (b) $C_3$-$C_8$-heterocycloalkyl and (c) $C_6$ to $C_{20}$ aromatic hydrocarbon and partially arene-hydrogenated forms, wherein each of (a)-(c) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms;
wherein said chiral catalyst is selected from the group consisting of chiral compounds (a) and (b), wherein the chiral compounds (a) are selected from the group consisting of chiral imidodiphosphates, and the chiral compounds (b) are selected from the group consisting of phosphoric acids, sulfonic acids, bisulfonimides, triflyl phosphoramides, and phosphinyl phosphoramides, said chiral compounds (b) comprising a catalytically active site [—(P,S)=O][—$NHR^E$, —OH], wherein $R^E$ is an electron-withdrawing group; and
wherein said imidodiphosphates have the formula (I):

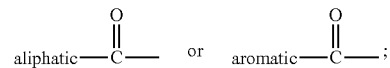

wherein:
X and Y are, independently from each other, the same or different and represent O, S, Se or $NR^N$;
$Z^1$ to $Z^4$ are, independently from each other, the same or different and represent O, S or $NR^N$;
n stands for 0 or 1;
W is a substituent being capable of forming a covalent or ionic bond with the imidodiphosphate moiety;
$R^1$ to $R^4$ are, independently from each other, the same or different and are each selected from the group consisting of aliphatic, heteroaliphatic, aromatic and heteroaromatic groups, each of which groups is optionally further substituted by one or more metal-free heterosubstituents, aliphatic, heteroaliphatic, aromatic or heteroaromatic groups, whereby
$R^1$ and $R^2$ form a ring system with P and, if present, $Z^1$ and $Z^2$, and $R^3$ and $R^4$ form a ring system with P and, if present, $Z^3$ and $Z^4$, respectively; and
$R^N$ is selected from the group consisting of (a) hydrogen, (b) $C_1$ to $C_{20}$ straight chain, branched chain or cyclic aliphatic hydrocarbons, optionally having one or more unsaturated bonds, (c) $C_3$-$C_8$-heterocycloalkyl and (d) $C_6$ to $C_{20}$ aromatic hydrocarbon and partially arene-hydrogenated forms, wherein each of (b)-(d) is optionally substituted by one or more groups selected from the group consisting of (i) $C_1$ to $C_{20}$ straight chain, branched chain or cyclic aliphatic hydrocarbons, optionally having one or more unsaturated bonds, (ii) $C_3$-$C_8$-heterocycloalkyl, and (iii) $C_6$ to $C_{20}$ aromatic hydrocarbon and partially arene-hydrogenated forms; and tautomeric and ionic forms of said imidodiphosphates.

* * * * *